United States Patent
Su et al.

(10) Patent No.: US 10,520,473 B2
(45) Date of Patent: Dec. 31, 2019

(54) DISTRIBUTED SENSING FIBER ACOUSTIC EMISSION FUSION SENSING SYSTEM AND RUNNING METHOD

(71) Applicant: HOHAI UNIVERSITY, Nanjing (CN)

(72) Inventors: Huaizhi Su, Nanjing (CN); Meng Yang, Nanjing (CN); Chongshi Gu, Nanjing (CN)

(73) Assignee: HOHAI UNIVERSITY, Nanjing (CN)

( * ) Notice: Subject to any disclaimer, the term of this patent is extended or adjusted under 35 U.S.C. 154(b) by 183 days.

(21) Appl. No.: 15/831,485

(22) Filed: Dec. 5, 2017

(65) Prior Publication Data

US 2019/0170698 A1  Jun. 6, 2019

(51) Int. Cl.
| | | |
|---|---|---|
| *G01N 29/14* | (2006.01) | |
| *G02B 6/02* | (2006.01) | |
| *G01N 29/32* | (2006.01) | |
| *G01N 29/24* | (2006.01) | |

(52) U.S. Cl.
CPC ......... *G01N 29/14* (2013.01); *G01N 29/2418* (2013.01); *G01N 29/326* (2013.01); *G02B 6/022* (2013.01); *G01N 2291/0258* (2013.01)

(58) Field of Classification Search
CPC ................................ G01N 29/14; G02B 6/022
See application file for complete search history.

(56) References Cited

U.S. PATENT DOCUMENTS

| | | | |
|---|---|---|---|
| 6,542,228 B1* | 4/2003 | Hartog | G01M 11/3127 356/73.1 |
| 10,209,060 B1* | 2/2019 | Nguyen | G01D 5/35316 |
| 2004/0035218 A1* | 2/2004 | Paulson | G01H 1/00 73/803 |
| 2010/0290734 A1* | 11/2010 | Kaplan | G01M 5/0091 385/12 |
| 2012/0125108 A1* | 5/2012 | Muravin | G01N 29/043 73/587 |
| 2015/0338380 A1* | 11/2015 | Ziehl | G01N 29/14 73/587 |
| 2019/0170697 A1* | 6/2019 | Su | G01N 29/14 |

* cited by examiner

*Primary Examiner* — Michael A Lyons
(74) *Attorney, Agent, or Firm* — Rankin, Hill & Clark LLP (57) ABSTRACT

A distributed sensing fiber acoustic emission fusion sensing system includes a sensing fiber temperature-sensitive compensation device and a sensing fiber acoustic emission demodulation device. A sensing fiber in the sensing fiber temperature-sensitive compensation device after being compensated enters the sensing fiber acoustic emission demodulation device.

9 Claims, 5 Drawing Sheets

DISTRIBUTED SENSING FIBER ACOUSTIC EMISSION FUSION SENSING SYSTEM AND RUNNING METHOD

TECHNICAL FIELD

The present invention relates to a distributed sensing fiber acoustic emission fusion sensing system and running method, and belongs to the field of hydraulic engineering structure safety monitoring and detecting.

BACKGROUND

Due to the invention of light and fiber, a remarkable success has been achieved in a fiber technology. Under the promotion of optical communication technology, great progress has been made in the research and development of all kinds of devices, such as optical fiber, devices, components, instruments and mechanical devices. As everyone knows, the optical wave is an electromagnetic wave; when the electromagnetic wave is emitted in a medium such as a fiber, the incident electromagnetic wave will interact with molecules or atoms forming the material, so as to generate scattering spectra, which commonly comprises Rayleigh scattering and Brillouin scattering. By using the scattered light information, people develop a lot of sensing fiber monitoring instruments. Since Mendes and other people firstly embedded a fiber sensor in a concrete structure to monitor the structure safety in 1989, scholars of all countries further promoted the application of the technology in construction and hydraulic engineering. At present, the fiber sensing technology has obtained some achievements on composite material solidification monitoring, nondestructive examination of structure, damage monitoring and identification and evaluation aspect.

In hydraulic engineering and civil engineering, the interior of the material may have fracture of different degrees under the effects of external temperature, water loading, weight, etc. The fracture is invisible internal damage under many conditions, and if the fracture cannot be detected and found in time, it is possible to develop into a potential safety hazard in the engineering. This defect or damage may have a continuously accumulated and irreversible process with the time, which may cause whole or partial sudden invalidation of the structure body, so as to lead to a serious engineering problem. The material may release elastic energy in damage, the elastic energy is transmitted in the form of elastic wave in the material, and the elastic wave is called an acoustic emission wave.

But regarding currently developed monitoring devices, the actual application of the fiber sensing technology lags far behind the requirement on the technology currently due of the variety of current performance parameters and the requirement of high standard, wherein the fusion sensing fiber technology and the acoustic emission technology are one of the fields lacking research. Since the sensing fiber technology and the acoustic emission technology have good monitoring and detecting performance, the fusion thereof will generate great technical improvement, so as to break through the piezoelectric ceramic acoustic emission detection method with a large system, many cables and bad anti-electronic logging interference ability and the current fiber bragg grating acoustic emission testing system of point mode monitoring.

SUMMARY

Object of the invention: in order to overcome the defects in the prior art, the present invention provides a distributed sensing fiber acoustic emission fusion sensing system and running method, which fuses a femtosecond laser optical frequency comb technology with an acoustic emission technology, and implements a monitoring and detecting technology with the advantages of spatial positioning, whole-process distribution, high spatial resolution and high detection accuracy by constructing a novel monitoring and detecting technology fusing the Rayleigh ejection scattering and Brillouin scattering optical fiber sensing technology with the acoustic emission technology. The present invention is novel in concept, simple in structure laying, is associated with convenient operation, and has better actual engineering application significance and scientific research value.

Technical solution: in order to solve the foregoing technical problems, the present invention provides a distributed sensing fiber acoustic emission fusion sensing system, which comprises a sensing fiber temperature-sensitive compensation device and a sensing fiber acoustic emission demodulation device, wherein a sensing fiber starts from the sensing fiber acoustic emission demodulation device, passes through the sensing fiber temperature-sensitive compensation device, and finally returns to the sensing fiber acoustic emission demodulation device, and the head and the tail of the sensing fiber in the sensing fiber temperature-sensitive compensation device need to be connected with the sensing fiber acoustic emission demodulation device.

The sensing fiber temperature-sensitive compensation device comprises a fiber-carrying guide module and a temperature-sensitive compensation module, a first sensing fiber, a second sensing fiber, and a third sensing fiber pass through the fiber-carrying guide module, the fiber-carrying guide module is provided with built-in fiber-fixing modules for fixing the first sensing fiber and the third sensing fiber, the first sensing fiber and the third sensing fiber are fixed by the built-in fiber-fixing modules and then disposed in parallel with the second sensing fiber; the first sensing fiber and the third sensing fiber are arranged on the upper surface of a circular arc-shaped housing, the second sensing fiber passes through the temperature compensation device and then is fixed on another fiber-carrying guide module, and the first sensing fiber the third sensing fiber are fixed on the fiber-carrying guide module through another pair of built-in fiber-fixing modules.

The sensing fiber acoustic emission demodulation device comprises a driving power source, a mode-locked laser, a femtosecond laser optical frequency comb, a pulse modulator, a wavelength division multiplexer, an optical path coupler, an amplifier, a receiver, a detector, a controller, a concrete structure safety behavior evaluation system, an acoustic emission signal, a Rayleigh optical receiver, a Brillouin optical receiver, and an optical splitter; the output end of the driving power source is connected with the input end of the mode-locked laser, the input end of the driving power source is connected with the output end of the controller, the mode-locked laser is connected with the femtosecond laser optical frequency comb, the pulse modulator and the wavelength division multiplexer in sequence, the output end of the wavelength division multiplexer is respectively connected with the input end of the optical splitter and the input end of the optical path coupler, the output end of the optical splitter is respectively connected with the input end of the Rayleigh optical receiver and the input end of the Brillouin optical receiver, the output end of the Rayleigh optical receiver and the output end of the Brillouin optical receiver are connected with the input end of the controller, the output end of the optical path coupler is connected with the input end of the amplifier and the input end of the receiver, the output end of the receiver is connected with the input end of the detector, the output end of the detector is connected with the input end of the controller, the output end of the amplifier is connected with a fiber acoustic emission sensing device, and the output end of the controller is connected with the concrete structure safety behavior evaluation system.

Preferably, the fiber acoustic emission sensing device comprises a base plate, and a first side plate and a second side plate fixedly connected with two sides of the base plate, the top portion of the first side plate is connected with the top portion of the second side plate through an arc-shaped fiber-carrying channel, and a main common cavity is formed by the base plate, the first side plate, the second side plate and the arc-shaped fiber-carrying channel; the top portions of the first side plate and the second side plate are respectively hinged with a first arc-shaped cover and a second arc-shaped cover, the lower end surface of the first arc-shaped cover is fixedly connected with a first arc-shaped pressing body, the lower end surface of the second arc-shaped cover is fixedly provided with a second arc-shaped pressing body, a fourth sensing fiber in the arc-shaped fiber-carrying channel is arranged under the first arc-shaped pressing body, a fifth sensing fiber is arranged under the second arc-shaped pressing body, and the first arc-shaped cover is connected with the second arc-shaped cover through a locking device; after the first arc-shaped cover and the second arc-shaped cover are rotated to tightly press the fourth sensing fiber and the fifth sensing fiber through the first arc-shaped pressing body and the second arc-shaped pressing body, the first arc-shaped cover and the second arc-shaped cover are locked through the locking device.

Preferably, a plurality of first through holes are arranged on the first side plate along the axis direction of the first sensing fiber, and a plurality of second through holes are arranged on the second side plate along the axis direction of the second sensing fiber.

Preferably, the first through hole is a common cavity circular hole, the section of the common cavity circular hole is a circular hole, the second through hole is a common cavity hexagonal hole, the section of the common cavity hexagonal hole is a hexagonal hole, and both the first through hole and the second through hole are in an odd number.

Preferably, the fiber-carrying guide module comprises a fiber holding-carrying table, an upper fiber-holding groove, a middle fiber-holding groove, a lower fiber-holding groove, a transition holding table section, an upper wedge-shaped holding table section and a lower wedge-shaped holding table section, wherein the upper fiber-holding groove, the middle fiber-holding groove and the lower fiber-holding groove are arranged in the fiber holding-carrying table from top to bottom in sequence, the first sensing fiber, the second sensing fiber and the third sensing fiber are fixed in the upper fiber-holding groove, the middle fiber-holding groove and the lower fiber-holding groove in sequence, and the fiber holding-carrying table is connected with the upper wedge-shaped holding table section and the lower wedge-shaped holding table section through the transition holding table section.

Preferably, the built-in fiber-fixing module comprises an upper arc end fastener, a lower arc end fastener, a fiber-locking thread column, an upper horizontal thread control column, a lower horizontal thread control column, a boss and a pair of sliding blocks; the boss is arranged on the upper wedge-shaped holding table section and the lower wedge-shaped holding table section, the boss is removably connected with the upper horizontal thread control column and the lower horizontal thread control column, the upper horizontal thread control column and the lower horizontal thread control column are in threaded connection with the pair of sliding blocks respectively, the fiber-locking thread column is in threaded connection with one of the sliding blocks, and the lower arc end fastener is fixedly connected with the other sliding block.

Preferably, the circular arc-shaped housing comprises three layers, the outermost layer is a special composite material layer, the middle layer is a metal compartment layer, and the innermost layer is an inner composite material layer.

Preferably, the temperature compensation apparatus comprises a pair of ellipsoids made of arc-shaped composite material, the two ellipsoids are arranged at the two ends of the circular arc-shaped housing, the ellipsoid is internally provided with a first fiber-feeding pipe for the second sensing fiber to pass through, a lageniform hoist body made of composite material is arranged between the two ellipsoids, the hoist body is internally provided with a second fiber-feeding pipe, the second sensing fiber passes through the first fiber-feeding pipe, the second fiber-feeding pipe and another first fiber-feeding pipe in sequence, and both the ellipsoids and the hoist body are supported in the circular arc-shaped housing through support columns.

A running method of the above distributed sensing fiber acoustic emission fusion sensing system comprises the following steps of:

first step: equipping three pieces of sensing fibers to be monitored as the first sensing fiber, the second sensing fiber and the third sensing fiber, preparing the circular arc-shaped housing, equipping the special composite material and the ellipsoids, and requiring the corresponding first sensing fiber and the third sensing fiber to pass through the special composite material layer, respectively passing the first sensing fiber, the second sensing fiber, and the third sensing fiber through the upper fiber-holding groove, the middle fiber-holding groove and the lower fiber-holding groove on the fiber holding-carrying table at the initial end of the sensing fiber temperature-sensitive compensation packaging device, and respectively injecting glue into the upper fiber-holding groove, the middle fiber-holding groove and the lower fiber-holding groove, fixing the initial ends of the three pieces of sensing fibers penetrated into the sensing fiber temperature-sensitive compensation packaging device, then transiting the first sensing fiber and the third sensing fiber to the transition holding table section by a certain radian, and packaging the first fiber-feeding pipe and the second fiber-feeding pipe;

second step: transiting the first sensing fiber to the boss by a 60-degree included angle with a horizontal plane, and injecting glue in the boss to fix the first sensing fiber again, driving the upper arc end fastener to move by the fiber-locking thread columns distributed at the head and tail ends, extending and fixing the first sensing fiber under a pre-tensioning stress, and injecting glue in the circular arc-shaped housing to lay the first sensing fiber into the special composite material layer contacted therewith, laying the second sensing fiber and the third sensing fiber in the same way, passing the first sensing fiber, the second sensing fiber and the third sensing fiber through the upper fiber-holding groove, the middle fiber-holding groove and the lower fiber-holding groove on the fiber holding-carrying table at the tail end of the sensing fiber temperature-sensitive compensation packaging device, and injecting glue in the upper fiber-holding groove, the middle fiber-holding groove and the lower fiber-holding groove, so as to complete a sensing fiber temperature-desensitized operation and embed the device to finally lay a sensing device;

third step: opening each member of the sensing fiber acoustic emission demodulation device and controlling the controller to start the driving power source, thus exciting the mode-locked laser to generate the femtosecond laser optical frequency comb, and then modulating the femtosecond laser optical frequency comb through the pulse modulator, the wavelength division multiplexer and the optical splitter;

fourth step: in order to remove the temperature interference more accurately, averaging strain values of the first sensing fiber and the third sensing fiber processed by an upper special composite material and a lower special composite material as the relatively accurate strain value of the sensing fiber acquired for the first time, then using the strain value of the second sensing fiber to amend the average value of the strain values of the first sensing fiber and the third sensing fiber as the final strain value monitored by the sensing fiber without the temperature interference; and fifth step: an acoustic emission signal being generated when some part of the structure to be monitored is damaged, the acoustic emission signal being transduced into the common cavity circular hole, the common cavity hexagonal hole and the main common cavity, and Rayleigh scattering light information and Brillouin scattering light information in the sensing fiber being affected, receiving and detecting the femtosecond laser optical frequency comb of the changed Rayleigh scattering light information and the changed Brillouin scattering light information through the Rayleigh optical receiver, the Brillouin optical receiver and the receiver, then collecting the information into the concrete structure safety behavior evaluation system through the controller for analysis and research, and evaluating and analyzing the information like the damaged position and degree of the structure.

Beneficial effects: according to the distributed sensing fiber acoustic emission fusion sensing system of the present invention, pure overlapping of the conventional simple technologies is broken through on the aspects of mechanism and practical engineering application; a femtosecond laser optical frequency comb technology is introduced and fused with an acoustic emission technology, and Rayleigh ejection scattering and Brillouin scattering are separated to sense acoustic emission waves in a grading way; a multi-device multi-module multi-component fusion system consisting of the sensing fiber temperature-sensitive compensation device, the fiber acoustic emission sensing device and the sensing fiber acoustic emission demodulation device has the advantages of spatial positioning, whole-process distribution, high spatial resolution, high detection accuracy, quantitative detection and the like. The present invention is complete in structure, is novel in concept, is simple in layout, is convenient to operate, can achieve process and automatic application, and has great advantages on the aspects of lowering the monitoring cost, increasing the monitoring accuracy, and improving the engineering practicability.

DETAILED DESCRIPTION

Figure 1:
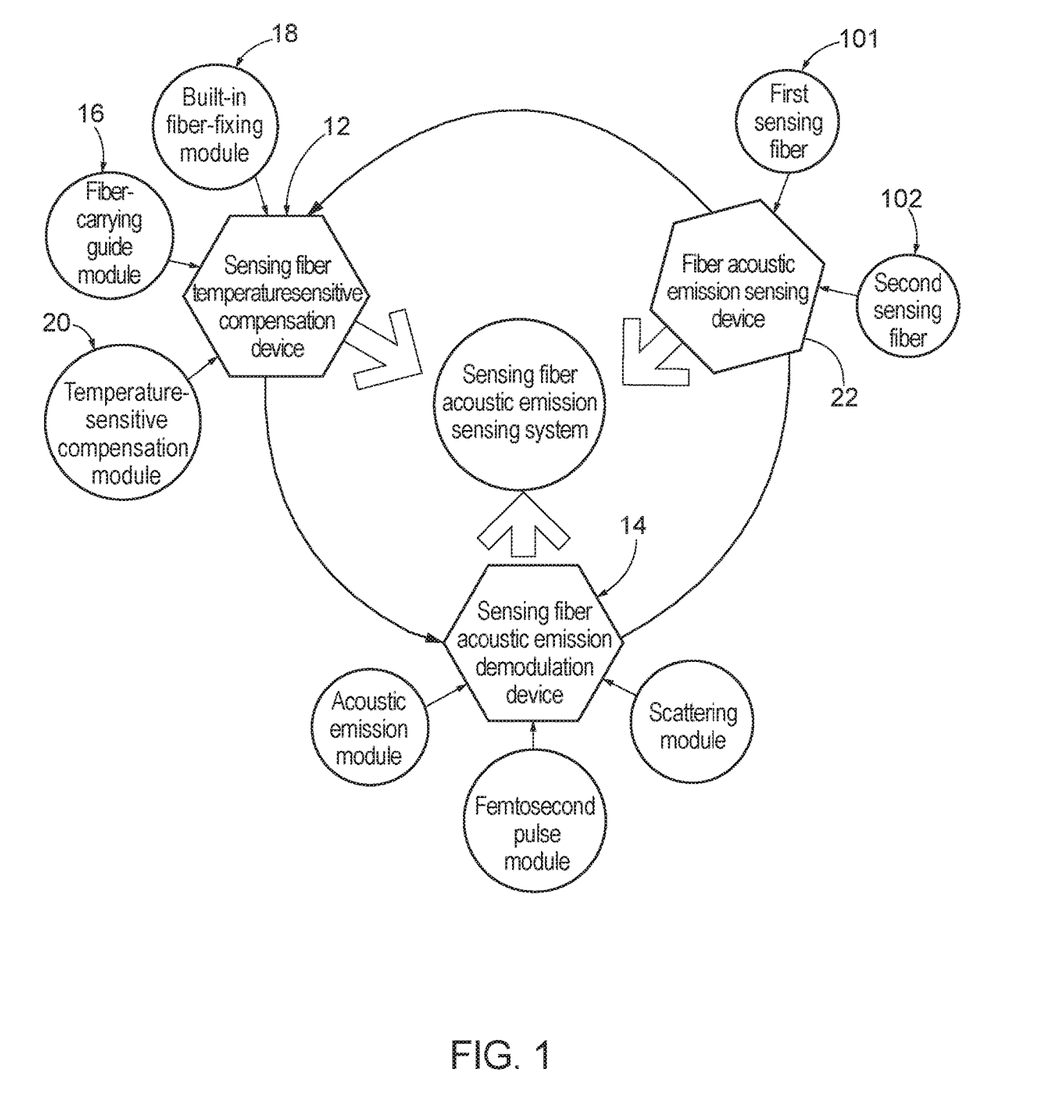
FIG. 1 is a structure diagram of the present invention.

As shown in FIG. 1 to FIG. 8, but with reference to FIG. 1, the invention discloses a distributed sensing fiber acoustic emission fusion sensing system 10, which comprises a sensing fiber temperature-sensitive compensation device 12 and a sensing fiber acoustic emission demodulation device 14, wherein a sensing fiber in the sensing fiber temperature-sensitive compensation device 12 after being compensated enters the sensing fiber acoustic emission demodulation device 14.

Figure 2:
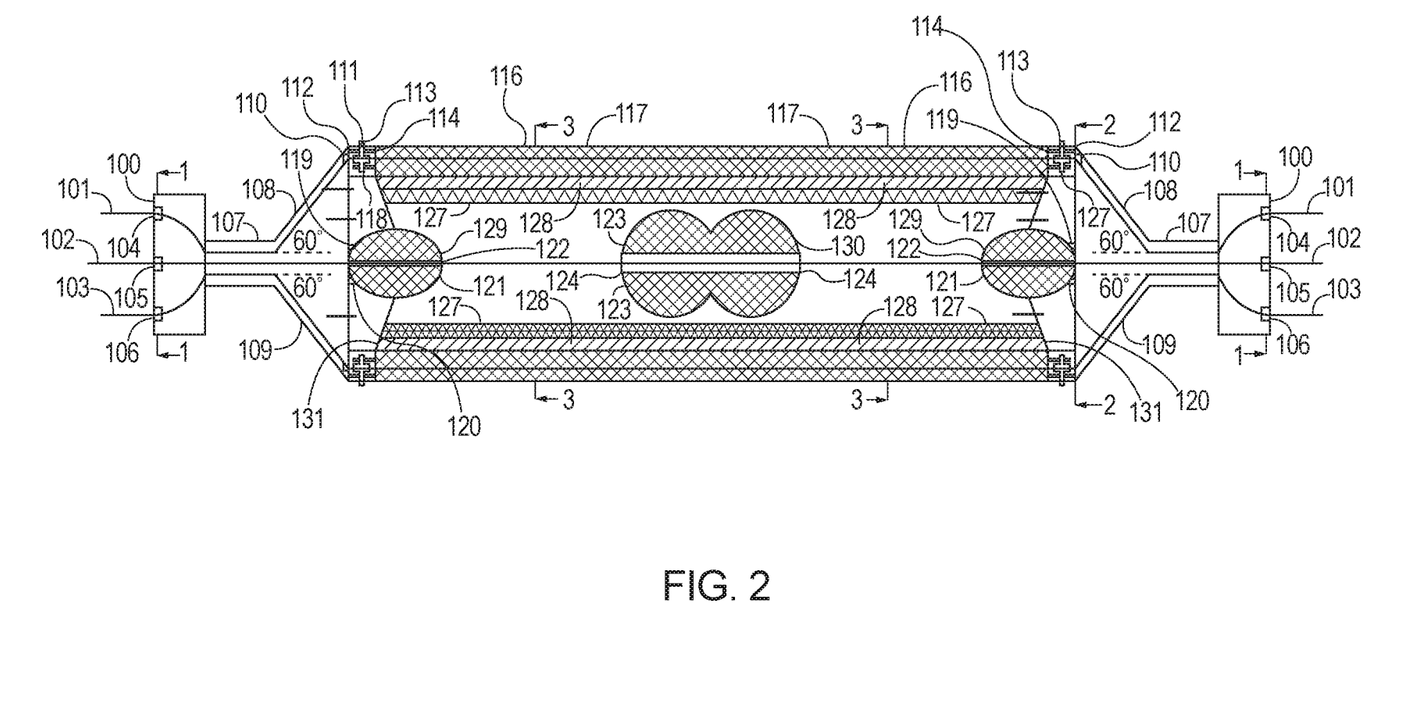
FIG. 2 is a structural schematic diagram of a sensing fiber temperature-sensitive compensation device in FIG. 1.
Figure 3:
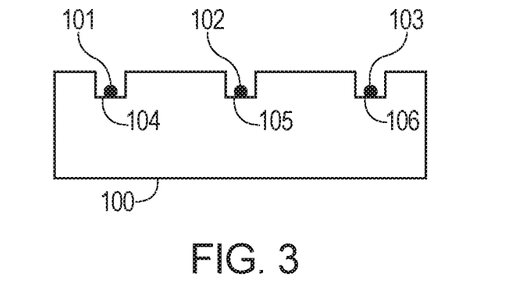
FIG. 3 is a structural schematic diagram of a 1-1 section in FIG. 2.
Figure 4:
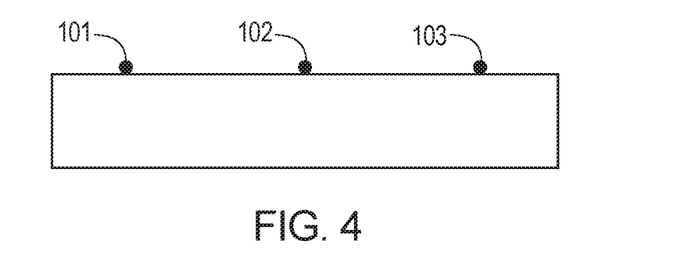
FIG. 4 is a structural schematic diagram of a 2-2 section in FIG. 2.
Figure 5:
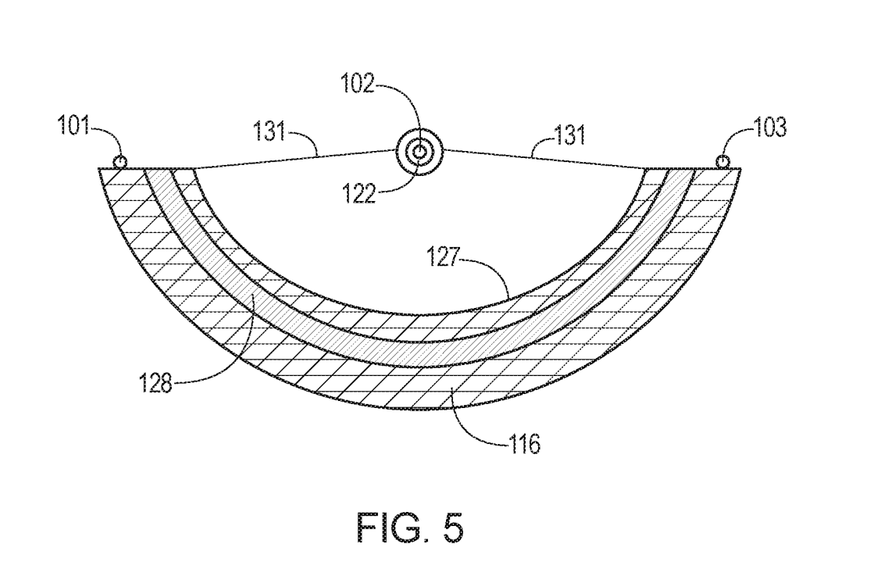
FIG. 5 is a structural schematic diagram of a 3-3 section in FIG. 2.

The sensing fiber temperature-sensitive compensation packaging system 12 of the present invention comprises a fiber-carrying guide module 16, a built-in fiber-fixing module 18 and a temperature-sensitive compensation module 20. With reference to FIG. 2, the fiber-carrying guide module 16 comprises a fiber holding-carrying table 100 with a length of 20 cm, a width of 10 cm wide and a height of 5 cm, an upper fiber-holding groove 104 with an opening groove depth of 2 cm, a middle fiber-holding groove 105 with an opening groove depth of 2 cm, a lower fiber-holding groove 106 with an opening groove depth of 2 cm, a transition holding table section 107 with a length of 10 cm, a width of 5 cm wide and a height of 3 cm, as well as an upper wedge-shaped holding table section 108 and a lower wedge-shaped holding table section 109 at a 60-degree included angle with a horizontal direction; wherein, the upper fiber-holding groove 104, the middle fiber-holding groove 105 and the lower fiber-holding groove 106 are laid in the fiber holding-carrying table 100 from top to bottom in sequence, the fiber holding-carrying table 100 is connected with the upper wedge-shaped holding table section 108 and the lower wedge-shaped holding table section 109 through the transition holding table section 107, and 518 instant glue is injected in the upper fiber-holding groove 104, the middle fiber-holding groove 105 and the lower fiber-holding groove 106 to fix a G.652D first sensing fiber 101, a G.652D second sensing fiber 102 and a G.652D third sensing fiber 103 in the fiber holding-carrying table 100 (e.g., seen in greater detail in FIGS. 3-4); the first sensing fiber 101 and the third sensing fiber 103 respectively pass through the upper wedge-shaped holding table section 108 and the lower wedge-shaped holding table section 109 at a 60-degree included angle with the horizontal plane.

Figure 6:
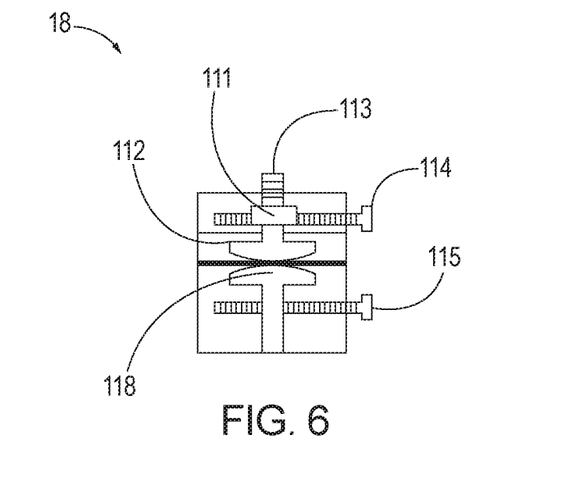
FIG. 6 is a detailed structural diagram of an upper arc end fastener in FIG. 2.

With reference to FIG. 6, the built-in fiber-fixing module 18 comprises an upper arc end fastener 112 with a thickness of 2 cm, a lower arc end fastener 118 with a thickness of 2 cm, a fiber-locking thread column 113 with a diameter of 1 cm and a length of 4 cm, an upper horizontal thread control column 114 with a length of 5 cm and a diameter of 1 cm, a lower horizontal thread control column 115 with a length of 5 cm and a diameter of 1 cm, a boss 110 and a pair of sliding blocks 111; the boss 110 is arranged on the upper wedge-shaped holding table section 108 and the lower wedge-shaped holding table section 109, the boss 110 is removably connected with the upper horizontal thread control column 114 and the lower horizontal thread control column 115, the upper horizontal thread control column 114 and the lower horizontal thread control column 115 can rotate only in the boss 110 and cannot move, the upper horizontal thread control column 114 and the lower horizontal thread control column 115 are in threaded connection with the pair of sliding blocks 110 respectively, the fiber-locking thread column 113 is in threaded connection with one of the sliding blocks 111, and the lower arc end fastener 118 is fixedly connected with the other sliding block 111. The upper horizontal thread control column 114 and the lower horizontal thread control column 115 are rotated to drive the sliding blocks 111 to move left and right, and the fiber-locking thread column 113 is screwed to drive the fiber-locking thread column 113 to remove up and down, thus driving the upper arc end fastener 112 to move and match with the lower arc end fastener 118 to lock the first sensing fiber 101 and the third sensing fiber 103.

The temperature-sensitive compensation module 20 comprises a circular arc-shaped housing 116 with a length of 40 cm, a height of 4 cm and an outer diameter of 15 cm, a special composite material layer 117, an inner composite material layer 127, a metal compartment layer 128, an upper-half arc-shaped composite material 129 with a length of 40 cm, a lower-half arc-shaped composite material 121, a first fiber-feeding pipe 122 with a diameter of 2 cm and a length of 15 cm, a left arc-shaped composite material 123, a right arc-shaped composite material 130, a second fiber-feeding pipe 124 with a diameter of 2 cm and a length of 25 cm, and an inner support column 131 with a length less than 20 cm; wherein, the circular arc-shaped housing 116 is internally equipped with the special composite material layer 117 made of special performance resin matrix composite material which is close to the metal compartment layer 128 made of chromium, the inside of the metal compartment layer 128 is close to the inner composite material layer 127 made of special performance resin matrix composite material, the inner composite material layer 127 is connected with the upper-half arc-shaped composite material 129 made of special performance resin matrix composite material and the lower-half arc-shaped composite material 121 made of special performance resin matrix composite material, the ellipsoid is formed by the upper-half arc-shaped composite material 129 and lower-half arc-shaped composite material 121, the first fiber-feeding pipe 122 with a diameter of 2 cm and a length of 15 cm is located in the middle position of the upper-half arc-shaped composite material 129 and the lower-half arc-shaped composite material 121, the second fiber-feeding pipe 124 with a diameter of 2 cm and a length of 25 cm is located in the middle position of the left arc-shaped composite material 123 made of special performance resin matrix composite material and the right arc-shaped composite material 130 made of special performance resin matrix composite material, the hoist body is formed by the left arc-shaped composite material 123 and the right arc-shaped composite material 130, and the product of the differences between the thermal expansion coefficient of the special composite material layer 117 made of special performance resin matrix composite material and the thermal expansion coefficient of the corresponding G.652D first sensing fiber 101 and the corresponding G.652D third sensing fiber 103 passing through the special composite material layer 117 with the strain value of the corresponding section of the first sensing fiber 101 and the third sensing fiber 103 is equal to the thermal coefficient of the corresponding section of the first sensing fiber 101 and the third sensing fiber 103.

Four built-in fiber-fixing modules 18 are configured in total, which are respectively located at the initial end of sensing fiber temperature-sensitive compensation packaging device; the positions for fixing the G.652D first sensing fiber 101 and the G.652D third sensing fiber 103 may be modulated through the four built-in fiber-fixing modules 18; a certain pre-tensioning stress is applied on the first sensing fiber 101 and the third sensing fiber 103 laid, the special composite material layer 117 made of special performance resin matrix composite material is isolated from the inner composite material layer 127 made of special performance resin matrix composite material by the metal compartment layer 128 made of chromium so as to make the part inside the inner composite material layer 127 to form an independent structure, the second sensing fiber 102 passes through the upper-half arc-shaped composite material 129 and the lower-half arc-shaped composite material 121 firstly, and then passes through the left arc-shaped composite material 123 and the right arc-shaped composite material 130, the upper-half arc-shaped composite material 129, the lower-half arc-shaped composite material 121, the left arc-shaped composite material and the right arc-shaped composite material 130 are all arranged in a cavity between the inner composite material layer 127 and the inner support column 131 (e.g., seen in greater detail in FIG. 5), and the product of the difference values between the thermal expansion coefficients of the upper-half arc-shaped composite material 129 and the lower-half arc-shaped composite material 121, the left arc-shaped composite material 123 and the right arc-shaped composite material 130, and the thermal expansion coefficient of the inner composite material layer 127 with the strain value of the corresponding section of the second sensing fiber 102 is equal to the thermal coefficient of the corresponding section of the second sensing fiber 102.

Figure 8:
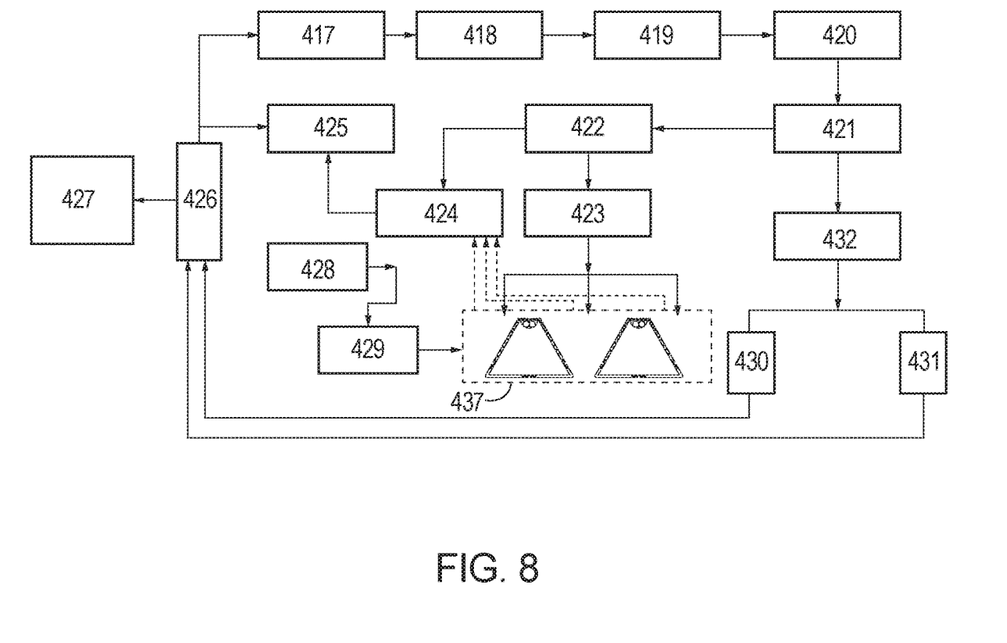
FIG. 8 is a structural schematic diagram of a sensing fiber acoustic emission demodulation device in FIG. 1.

With reference to FIG. 8, the input end of a driving power source 417 in the sensing fiber acoustic emission demodulation device 14 is connected with the output end of a controller 426, the output end of the driving power source 417 is connected with the input end of a mode-locked laser 418, the light information output end of the mode-locked laser 418 is connected with a femtosecond laser optical frequency comb 419, the output end of the femtosecond laser optical frequency comb 419 is connected with the input end of a pulse modulator 420, the output end of the pulse modulator 420 is connected with the input end of a wavelength division multiplexer 421, the output end of the wavelength division multiplexer 421 is connected with the input end of the optical splitter 432 and the input end of an optical path coupler 422, the output end of the optical splitter 432 is respectively connected with the input end of a Rayleigh optical receiver 430 and the input end of a Brillouin optical receiver, the output end of the Rayleigh optical receiver 430 and the output end of the Brillouin optical receiver 431 are connected with the input end of a controller 426, the output end of the optical path coupler 422 is connected with the input end of an amplifier 423 and the input end of a receiver 424, the output end of the receiver 424 is connected with the input end of a detector 425, the output end of the amplifier 423 is connected with a GJJV tight-buffered sensing fiber in the fiber acoustic emission sensing device 22, and the output end of the controller 426 is connected with a concrete structure safety behavior evaluation system 427.

Figure 7:
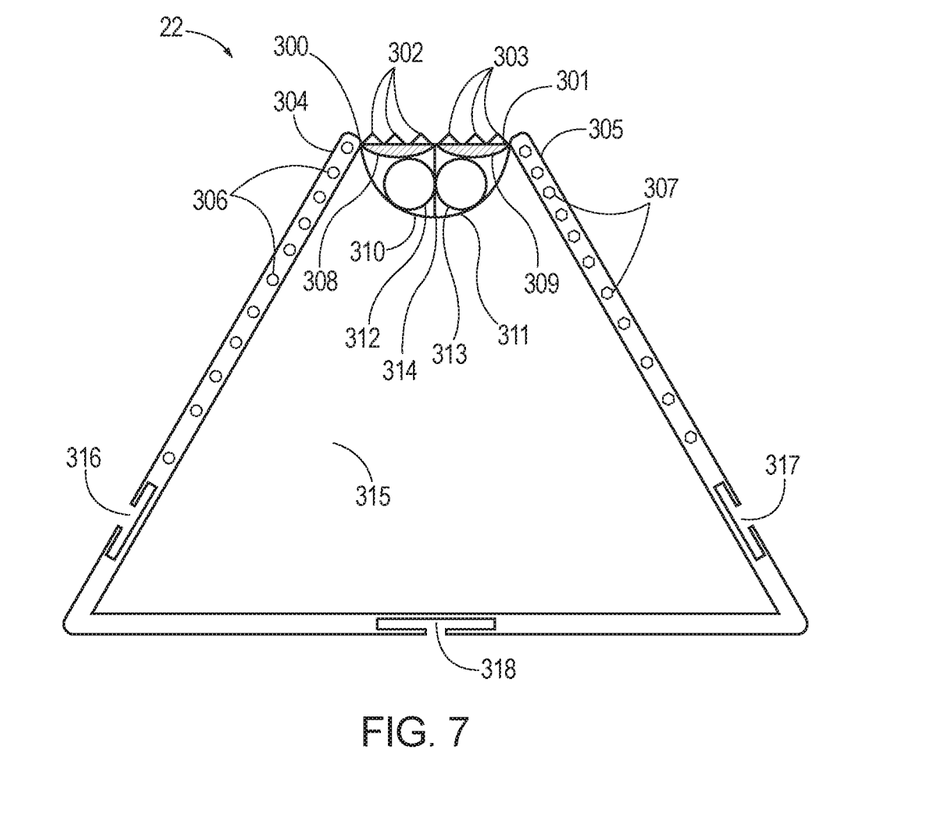
FIG. 7 is a structural schematic diagram of a fiber acoustic emission sensing device in FIG. 1.

With reference to FIG. 7, the fiber acoustic emission sensing device 22 comprises a base plate, and a first side plate 304 and a second side plate 305 fixedly connected with two sides of the base plate, the top portion of the first side plate 304 is connected with the top portion of the second side plate 305 through an arc-shaped fiber-carrying channel, the arc-shaped fiber-carrying channel comprises a first arc-shaped fiber-carrying channel 310 first arc-shaped fiber-carrying channel with a radian of $\pi/2$ and a 3 second arc-shaped fiber-carrying channel 311 with a radian of $\pi/2$, and a main common cavity 315 is formed by the base plate, the first side plate 304, the second side plate 305 and the arc-shaped fiber-carrying channel; the top portions of the first side plate 304 and the second side plate 305 are respectively hinged with a first arc-shaped cover 300 and a second arc-shaped cover 301, the lower end surface of the first arc-shaped cover 300 is fixedly connected with a first arc-shaped pressing body 308, the lower end surface of the second arc-shaped cover 301 is fixedly provided with a second arc-shaped pressing body 309, a first sensing fiber 312 in the arc-shaped fiber-carrying channel is arranged under the first arc-shaped pressing body 308, a second sensing fiber 313 is arranged under the second arc-shaped pressing body 309, and the first arc-shaped cover 300 is connected with the second arc-shaped cover 301 through a locking device; after the first arc-shaped cover 300 and the second arc-shaped cover 301 are rotated to tightly press the first sensing fiber 312 and the second sensing fiber 313 through the first arc-shaped pressing body 308 and the second arc-shaped pressing body 309, the first arc-shaped cover 300 and the second arc-shaped cover 301 are locked through the locking device, wherein the locking device may either be a connecting piece like a screw and a bolt, or be a snap. The first arc-shaped pressing body 308 and the second arc-shaped pressing body 309 are strip-shaped bosses, and the section of the boss is circular-arc shaped. The right side of the second arc-shaped cover is closed to the second side plate; in order to produce a symmetrical acoustic emission effect, an odd number of common cavity hexagonal holes are arranged on the upper end of the second side plate, and the number of the common cavity hexagonal holes is 11; in order to generate a difference with a common cavity circular hole on the first side plate while spreading acoustic emission waves, the common cavity hexagonal hole on the second side plate is in a regular hexagon shape; in order to order to realize the resonance of the acoustic emission transmission at a better angle, the information may be transferred to the sensing fiber by preferably utilizing the resonance of the acoustic emission source with the common cavity circular hole and the main common cavity.

The bottom end of a normal triple prism-shaped left convex corner 302 of a regular triangle with a side length of 2 cm is connected with the top end surface of the first arc-shaped cover 300 with a length of 5 cm and a width of 1 cm, wherein the left convex corner 302 is mainly used to add friction with a structure to be monitored when embedding the device, so as to enhance a coordination deformation capacity between the device and the structure to be monitored; the first arc-shaped cover 300 may be rotated to drive the first arc-shaped pressing body 308 to move, the top end surface of the first arc-shaped pressing body 308 with a radian of $\pi/3$ is connected with the first arc-shaped cover 300 with a length of 5 cm and a width of 1 cm, the first arc-shaped fiber-carrying channel with a radian of $\pi/2$ and a radius of 5 cm in a circular arc-shape, a channel-carrying diaphragm 314 with a length of 5 cm and the first arc-shaped pressing body 308 with a radian of $\pi/3$ constitute a triangle structure, the first arc-shaped pressing body 308 is connected with the first arc-shaped fiber-carrying channel, and the triangle structure may effectively fix the GJJV first tight-buffered sensing fiber 312. 11 common cavity circular holes 306 with a diameter of 3 cm and a circular section are totally configured in the embodiment. The 11 common cavity circular holes 306 are distributed in the first side plate 304 with a length of 20 cm and a width of 5 cm at an interval of 1 cm, the first side plate 304 forms a 60-degree included angle with the horizontal plane, the first side plate 304 is connected with the first arc-shaped fiber-carrying channel 310, the middle and lower portion of the first side plate 304 is provided with a first external groove 316 with an opening having a height of 2 cm and a width of 4 cm, and the first external groove 316 is a I-shaped opening which can reduce the interference when the device is embedded.

In the present invention, the second arc-shaped cover 301 has a length of 5 cm and a width of 1 cm is connected with a triple prism-shaped right convex corner 303 of the regular triangle with a side length of 2 cm, the second side plate 305 has a length of 20 cm and a width of 5 cm, the section of the common cavity hexagonal hole 307 is an equilateral hexagon, a second external groove 317 has a side length of 1 cm and an opening having a height of 2 cm and a width of 4 cm, the second arc-shaped pressing body 309 has a radian of $\pi/3$, the second arc-shaped fiber-carrying channel 311 is in a circular arc-shaped type with a radian of $\pi/2$ and a radius of 5 cm for the GJJV second tight-buffered sensing fiber 313. The GJJV second tight-buffered sensing fiber 313 is laid in the second arc-shaped fiber-carrying channel 311 in a circular arc-shaped type with a radian of $\pi/2$ and a radius of 5 cm, the top edge of the second arc-shaped pressing body 309 with a radian of $\pi/3$ is connected with the bottom end of the second arc-shaped cover 301 with a length of 5 cm and a width of 1 cm, the top end surface of the second arc-shaped cover 301 with a length of 5 cm and a width of 1 cm is connected with the bottom end surface of the right convex corner 303 with a length of 5 cm and a width of 1 cm, the right edge of the second arc-shaped cover 301 with a length of 5 cm and a width of 1 cm is connected with the second side plate 305 with a length of 20 cm and a width of 5 cm, the second arc-shaped cover 301 with a length of 5 cm and a width of 1 cm, which serves as a carrier of the right convex corner 303, also presses the second arc-shaped pressing body 309 with a radian of $\pi/3$ in the second arc-shaped fiber-carrying channel 311, the bulge arrangement of the second arc-shaped pressing body 309 is utilized to press the GJJV second tight-buffered sensing fiber 313 to the position close to the channel-carrying diaphragm, the second side plate 305 with a length of 20 cm and a width of 5 cm is provided with common cavity hexagonal holes 307 with equal sizes, an equilateral hexagon section and a side length of 1 cm from top to bottom in sequence, 11 common cavity hexagonal holes 307 are laid on the upper end of the second side plate 305, the second side plate 305 forms a 60-degree included angle with the horizontal plane, and the second external groove 317 and a bottom external groove 318 having an opening with a height of 1 cm and a weight of 5 cm are I-shaped openings, which can reduce the interference when the device is embedded.

A running method of the above distributed sensing fiber acoustic emission fusion sensing system 10 comprises the following steps.

(1) Determine a Region to be Monitored, Equip Members and Assemble Modules

A 150 m×100 m region with a perimeter of 500 m in some upstream face of some region to be monitored of a concrete dam in the northwest is selected as example in the embodiment. In view of considering possible bending and a line leading purpose, it is finally determined that three pieces of G.652D sensing fibers with a length of 600 m are used as the first sensing fiber 101, the second sensing fiber 102 and the third sensing fiber 103, wherein the members of the distributed sensing fiber acoustic emission fusion sensing system 10 are equipped and the modules in each device are assembled according to an order of from the sensing fiber temperature-sensitive compensation device 12 to the sensing fiber acoustic emission demodulation device 14.

Because the basic demodulation principle of the present invention is to use the Brillouin scattering technology which requires a closed loop, i.e., the sensing fiber has to start from the sensing fiber acoustic emission demodulation device 14, pass through the sensing fiber temperature-sensitive compensation device 12, and finally return to the sensing fiber acoustic emission demodulation device 14, and the head and tail of the sensing fiber in the sensing fiber temperature-sensitive compensation device 12 needs to be connected with the sensing fiber acoustic emission demodulation device 14.

(2) Close the Device, and Conduct Initial Running Debugging

The first G.652D sensing fiber 101 is respectively passed through the upper fiber-holding groove 104, the transition holding table section 107, the boss 110, the lower arc end fastener 118 and the circular arc-shaped housing 116; moreover, glue is injected in the upper fiber-holding groove 104 and the boss 110 to fix the initial end, then the upper arc end fastener 112 and the lower arc end fastener 118 are moved to a position closer to the boss 110 by adjusting the lower horizontal thread control column 115 and the upper horizontal thread control column 114, then the fiber-locking thread column 113 is rotated to set a pre-tensioning stress of the upper arc end fastener 112; the third sensing fiber 103 is laid on the transition holding table section 107 and the lower wedge-shaped holding table section 109 by using the same operation method, and the second sensing fiber 102 is mainly guided to the first fiber-feeding pipe 122 and the second fiber-feeding pipe 124; in addition, the first fiber-feeding pipe 122 and the second fiber-feeding pipe 124 are packed; initial running debugging is conducted, the average value of the strain values of the first sensing fiber 101 and the third sensing fiber 103 are amended by using the strain value of the second sensing fiber 102, so as to determine the most reliable numerical value of the strain monitored by the temperature interference-free sensing fiber.

(3) Embed the Device to Finish Laying

The first arc-shaped cover 300 with a length of 5 cm and a width of 1 cm and the second arc-shaped cover 301 with a length of 5 cm and a width of 1 cm may be rotated to drive the first arc-shaped pressing body 308 with a radian of $\pi/3$ and the second arc-shaped pressing body 309 with a radian of $\pi/3$ to move, a triangle layout form is formed by the first arc-shaped pressing body 308 with a radian of $\pi/3$, the first arc-shaped fiber-carrying channel 310 with a radian of $\pi/2$ and a radius of 5 cm in a circular arc-shaped type, and the channel-carrying diaphragm 314 with a length of 5 cm, and a triangle layout form is formed by the second arc-shaped pressing body 309 with a radian of $\pi/3$, the second arc-shaped fiber-carrying channel 311 with a radian of $\pi/2$ and a radius of 5 cm in a circular arc-shaped type, and the channel-carrying diaphragm 314 with a length of 5 cm; moreover, the first arc-shaped pressing body 308 with a radian of $\pi/3$ and the second arc-shaped pressing body 309 with a radian of $\pi/3$ are structures bulged in the middle, which can fix the first G.652D sensing fiber 101 and the third sensing fiber 103 in a non-rigid manner; the first external groove 316 with an opening having a height of 2 cm and a width of 4 cm, the second external groove 317 with an opening having a height of 2 cm and a width of 4 cm and the bottom external groove 318 with an opening having a height of 1 cm and a width of 5 cm are respectively passed through a steel bar component in the structure to be monitored to complete the basic laying procedure; the first sensing fiber 101 and the third sensing fiber 103 start from the sensing fiber acoustic emission demodulation device 14, pass through the sensing fiber temperature-sensitive compensation device 12, and finally return to the sensing fiber acoustic emission demodulation device 14, and the head and tail of the sensing fiber in the sensing fiber temperature-sensitive compensation device 12 need to be connected with the sensing fiber acoustic emission demodulation device 14.

(4) Turn on a Switch to Monitor Initial Values

The driving power source 417 is started through controlling the controller 426, so that the mode-locked laser 418 is stimulated to generate the femtosecond laser optical frequency comb 419, the femtosecond laser optical frequency comb 419 is modulated through the pulse modulator 420, the wavelength division multiplexer 421 and the optical splitter 432, and the femtosecond laser optical frequency combs 419 of the changed Rayleigh scattering light information and the changed Brillouin scattering light information can be received and detected through the detector 425, the Rayleigh optical receiver 430, the Brillouin optical receiver 431 and the receiver 424, and are used as the initial light information reference value of the region to be monitored.

(5) Conduct Dynamic Monitoring and Analysis

An acoustic emission signal 429 is generated when some part of the structure is damaged, the acoustic emission signal transmitted through the pentagon common cavity mesh, the triangle common cavity mesh, the circular common cavity mesh and the quadrangle common cavity mesh may be transduced into the G.652D tight-buffered sensing fiber of the fiber-carrying laying module 437 according to different time and frequencies, Rayleigh scattering light information and Brillouin scattering light information in the G.652D tight-buffered sensing fiber may be changed, the changed Rayleigh scattering light information and Brillouin scattering light information are collected into the concrete structure safety behavior evaluation system 427 through the controller 426, and are analyzed and compared with the result of step (4), to evaluate the damage degree 428 and position of the structure and realize e dynamic monitoring. The description above is only the preferable embodiment of the present invention, and it should be noted that those skilled in the art may make a plurality of improvements and decorations without departing from the principle of the present invention, and these improvements and decorations shall also fall within the protection scope of the present invention.

The invention claimed is:

1. A distributed sensing fiber acoustic emission fusion sensing system, comprising a sensing fiber temperature-sensitive compensation device and a sensing fiber acoustic emission demodulation device, wherein a sensing fiber starts from the sensing fiber acoustic emission demodulation device, passes through the sensing fiber temperature-sensitive compensation device, and finally returns to the sensing fiber acoustic emission demodulation device, and a head and a tail of the sensing fiber in the sensing fiber temperature-sensitive compensation device need to be connected with the sensing fiber acoustic emission demodulation device;

the sensing fiber temperature-sensitive compensation device comprises a fiber-carrying guide module and a temperature-sensitive compensation module, a first sensing fiber, a second sensing fiber and a third sensing fiber pass through the fiber-carrying guide module, the fiber-carrying guide module is provided with built-in fiber-fixing modules for fixing the first sensing fiber and the third sensing fiber, the first sensing fiber and the third sensing fiber are fixed by the built-in fiber-fixing modules and then disposed in parallel with the second sensing fiber;

the first sensing fiber and the third sensing fiber are arranged on an upper surface of a circular arc-shaped housing, the second sensing fiber passes through the temperature compensation device and then is fixed on a second fiber-carrying guide module, and the first sensing fiber the third sensing fiber are fixed on the fiber-carrying guide module through a second pair of built-in fiber-fixing modules; and the sensing fiber acoustic emission demodulation device comprises a driving power source, a mode-locked laser, a femtosecond laser optical frequency comb, a pulse modulator, a wavelength division multiplexer, an optical path coupler, an amplifier, a receiver, a detector, a controller, a concrete structure safety behavior evaluation system, an acoustic emission signal, a Rayleigh optical receiver, a Brillouin optical receiver, and an optical splitter;

an output end of the driving power source is connected with an input end of the mode-locked laser, an input end of the driving power source is connected with an output end of the controller, the mode-locked laser is connected with the femtosecond laser optical frequency comb, the pulse modulator and the wavelength division multiplexer in sequence, an output end of the wavelength division multiplexer is respectively connected with an input end of the optical splitter and an input end of the optical path coupler, an output end of the optical splitter is respectively connected with an input end of the Rayleigh optical receiver and an input end of the Brillouin optical receiver, an output end of the Rayleigh optical receiver and an output end of the Brillouin optical receiver are connected with an input end of the controller, an output end of the optical path coupler is connected with an input end of the amplifier and an input end of the receiver, an output end of the receiver is connected with an input end of the detector, an output end of the detector is connected with the input end of the controller, an output end of the amplifier is connected with a fiber acoustic emission sensing device, and the output end of the controller is connected with the concrete structure safety behavior evaluation system.

2. The distributed sensing fiber acoustic emission fusion sensing system according to claim 1, wherein the fiber acoustic emission sensing device comprises a base plate, and a first side plate and a second side plate fixedly connected with two sides of the base plate, a top portion of the first side plate is connected with a top portion of the second side plate through an arc-shaped fiber-carrying channel, and a main common cavity is formed by the base plate, the first side plate, the second side plate and the arc-shaped fiber-carrying channel;

the top portions of the first side plate and the second side plate are respectively hinged with a first arc-shaped cover and a second arc-shaped cover, a lower end surface of the first arc-shaped cover is fixedly connected with a first arc-shaped pressing body, a lower end surface of the second arc-shaped cover is fixedly provided with a second arc-shaped pressing body, a fourth sensing fiber in the arc-shaped fiber-carrying channel is arranged under the first arc-shaped pressing body, a fifth sensing fiber is arranged under the second arc-shaped pressing body, and the first arc-shaped cover is connected with the second arc-shaped cover through a locking device;

after the first arc-shaped cover and the second arc-shaped cover are rotated to tightly press the fourth sensing fiber and the fifth sensing fiber through the first arc-shaped pressing body and the second arc-shaped pressing body, the first arc-shaped cover and the second arc-shaped cover are locked through the locking device.

3. The distributed sensing fiber acoustic emission fusion sensing system according to claim 2, wherein a plurality of first through holes are arranged on the first side plate along an axis direction of the first sensing fiber running along a length of the first sensing fiber, and a plurality of second through holes are arranged on the second side plate along an axis direction of the second sensing fiber running along a length of the second sensing fiber.

4. The distributed sensing fiber acoustic emission fusion sensing system according to claim 3, wherein the first through hole is a common cavity circular hole, a cross-section of the common cavity circular hole is a circular hole, the second through hole is a common cavity hexagonal hole, a cross-section of the common cavity hexagonal hole is a hexagonal hole, the plurality of first through holes are odd in number, and the plurality of second through holes are odd in number.

5. The distributed sensing fiber acoustic emission fusion sensing system according to claim 1, wherein the fiber-carrying guide module comprises a fiber holding-carrying table, an upper fiber-holding groove, a middle fiber-holding groove, a lower fiber-holding groove, a transition holding table section, an upper wedge-shaped holding table section and a lower wedge-shaped holding table section, wherein the upper fiber-holding groove, the middle fiber-holding groove and the lower fiber-holding groove are arranged in the fiber holding-carrying table from top to bottom in sequence, the first sensing fiber, the second sensing fiber and the third sensing fiber are fixed in the upper fiber-holding groove, the middle fiber-holding groove and the lower fiber-holding groove in sequence, and the fiber holding-carrying table is connected with the upper wedge-shaped holding table section and the lower wedge-shaped holding table section through the transition holding table section.

6. The distributed sensing fiber acoustic emission fusion sensing system according to claim 5, wherein the built-in fiber-fixing module comprises an upper arc end fastener, a lower arc end fastener, a fiber-locking thread column, an upper horizontal thread control column, a lower horizontal thread control column, a boss and a pair of sliding blocks;

the boss is arranged on the upper wedge-shaped holding table section and the lower wedge-shaped holding table section, the boss is removably connected with the upper horizontal thread control column and the lower horizontal thread control column, the upper horizontal thread control column and the lower horizontal thread control column are in threaded connection with the pair of sliding blocks respectively, the fiber-locking thread column is in threaded connection with one of the sliding blocks, and the lower arc end fastener is fixedly connected with the other sliding block.

7. The distributed sensing fiber acoustic emission fusion sensing system according to claim 6, wherein the circular arc-shaped housing comprises three layers, an outermost layer is a special composite material layer, a middle layer is a metal compartment layer, and an innermost layer is an inner composite material layer.

8. The distributed sensing fiber acoustic emission fusion sensing system according to claim 7, wherein the temperature-sensitive compensation module comprises a pair of ellipsoids made of arc-shaped composite material, the two ellipsoids are arranged at the two ends of the circular arc-shaped housing, one of the two ellipsoids is internally provided with a first fiber-feeding pipe for the second sensing fiber to pass through, a lageniform hoist body made of composite material is arranged between the two ellipsoids, the hoist body is internally provided with a second fiber-feeding pipe, the second sensing fiber passes through the first fiber-feeding pipe, the second fiber-feeding pipe and a third fiber-feeding pipe in sequence, and both the ellipsoids and the hoist body are supported in the circular arc-shaped housing through support columns.

9. A running method of the distributed sensing fiber acoustic emission fusion sensing system according to claim 8, comprising:

first step: equipping three pieces of sensing fibers to be monitored as the first sensing fiber, the second sensing fiber and the third sensing fiber, preparing the circular arc-shaped housing, equipping the special composite material and the ellipsoids, and requiring the first sensing fiber and the third sensing fiber to pass through the special composite material layer, respectively passing the first sensing fiber, the second sensing fiber and the third sensing fiber through the upper fiber-holding groove, the middle fiber-holding groove and the lower fiber-holding groove on the fiber holding-carrying table at an initial end of a sensing fiber temperature-sensitive compensation packaging device, and respectively injecting glue into the upper fiber-holding groove, the middle fiber-holding groove and the lower fiber-holding groove, fixing the initial ends of the three pieces of sensing fibers penetrated into the sensing fiber temperature-sensitive compensation packaging device, then transiting the first sensing fiber and the third sensing fiber to the transition holding table section by a certain radian, and packaging the first fiber-feeding pipe and the second fiber-feeding pipe;

second step: transiting the first sensing fiber to the boss by a 60-degree included angle with a horizontal plane, and injecting glue in the boss to fix the first sensing fiber again, driving the upper arc end fastener to move by the fiber-locking thread columns distributed at head and tail ends, extending and fixing the first sensing fiber under a pre-tensioning stress, and injecting glue in the circular arc-shaped housing to lay the first sensing fiber into the special composite material layer contacted therewith, laying the second sensing fiber and the third sensing fiber in the same way, passing the first sensing fiber, the second sensing fiber and the third sensing fiber through the upper fiber-holding groove, the middle fiber-holding groove and the lower fiber-holding groove on the fiber holding-carrying table at the tail end of the sensing fiber temperature-sensitive compensation packaging device, and injecting glue in the upper fiber-holding groove, the middle fiber-holding groove and the lower fiber-holding groove, so as to complete a sensing fiber temperature-desensitized operation and embed the sensing fiber temperature-sensitive compensation device to finally lay a sensing device;

third step: opening each member of the sensing fiber acoustic emission demodulation device and controlling the controller to start the driving power source, thus exciting the mode-locked laser to generate the femtosecond laser optical frequency comb, and then modulating the femtosecond laser optical frequency comb through the pulse modulator, the wavelength division multiplexer and the optical splitter;

fourth step: in order to remove a temperature interference more accurately, averaging strain values of the first sensing fiber and the third sensing fiber processed by an upper special composite material and a lower special composite material as a relatively accurate strain value of the first and third sensing fibers acquired for a first time, then using a strain value of the second sensing fiber to amend an average value of strain values of the first sensing fiber and the third sensing fiber as a final strain value monitored by the first and third sensing fibers without the temperature interference; and fifth step: the acoustic emission signal being generated when some part of a structure to be monitored is damaged, the acoustic emission signal being transduced into a common cavity circular hole, a common cavity hexagonal hole and a main common cavity, and Rayleigh scattering light information and Brillouin scattering light information in an affected sensing fiber, receiving and detecting the femtosecond laser optical frequency comb of a changed Rayleigh scattering light information and a changed Brillouin scattering light information through the Rayleigh optical receiver, the Brillouin optical receiver and the receiver, then collecting information including Rayleigh scattering light information and the Brillouin scattering light information into the concrete structure safety behavior evaluation system through the controller for analysis and research, and evaluating and analyzing the information for a damaged position and a degree of the structure.

\* \* \* \* \*